(12) United States Patent
Snell (10) Patent No.: US 8,315,884 B2
(45) Date of Patent: Nov. 20, 2012

(54) PRE-SELECTION DISPLAY OF ALERTS IN AN ORDER ENTRY SYSTEM

(75) Inventor: James Snell, Edinburgh (GB)

(73) Assignee: Microsoft Corporation, Redmond, WA (US)

( * ) Notice: Subject to any disclaimer, the term of this patent is extended or adjusted under 35 U.S.C. 154(b) by 361 days.

(21) Appl. No.: 12/351,868

(22) Filed: Jan. 12, 2009

(65) Prior Publication Data
US 2010/0176943 A1   Jul. 15, 2010

(51) Int. Cl.
*G06Q 10/00* (2012.01)
(52) U.S. Cl. .......................... 705/2; 340/573.1
(58) Field of Classification Search .................. 705/2, 3, 705/26; 340/573.1, 519, 539.12, 691.6, 540
See application file for complete search history.

(56) References Cited

U.S. PATENT DOCUMENTS

| | | |
|---|---|---|
| 6,014,631 A | 1/2000 | Teagarden et al. |
| 6,421,650 B1 * | 7/2002 | Goetz et al. ............... 705/3 |
| 2001/0001144 A1 * | 5/2001 | Kapp ............... 705/3 |
| 2002/0035484 A1 | 3/2002 | Mccormick |
| 2002/0143582 A1 | 10/2002 | Neuman et al. |
| 2005/0144038 A1 | 6/2005 | Tamblyn et al. |
| 2006/0265245 A1 * | 11/2006 | McCallie et al. ............... 705/2 |
| 2007/0067186 A1 | 3/2007 | Brenner et al. |
| 2008/0262870 A1 | 10/2008 | Jones et al. |

FOREIGN PATENT DOCUMENTS
WO    2008006203 A1    1/2008

OTHER PUBLICATIONS

Lamy, et al., "Design of a graphical and interactive interface for facilitating access to drug contraindications,cautions for use, interactions and adverse effects," retrieved at <<http://www.pubmedcentral.nih.gov/articlerender.fcgi?artid=2442832>>, Jun. 2, 2008, 14 pages.

Lamy, et al., "An iconic language for the graphical representation of medical concepts," retrieved at <<http://www.biomedcentral.com/1472-6947/8/16>>, Apr. 24, 2008, 15 pages.

Scalise, Dagmara, "The Case for E-Prescribing," retrieved at <<http://www.hhnmag.com/hhnmag_app/jsp/articledisplay.jsp?dcrpath=HHNMAG/Article/data/02FEB2007/0702HHN_FEA_Gatefold&domain=HHNMAG>>, Dec. 16, 2008, 4 pages.

* cited by examiner

*Primary Examiner* — Thomas Mullen (57) ABSTRACT

An order entry system is described which displays items together with visual attributes that correspond to respective alerts. The visual attributes provide pre-selection guidance to a user in choosing from among the items without deluging the user with a cumbersome series of post-selection alerts. In one illustrative case, the items that are displayed correspond to drug-related items. In this case, one purpose of the order-entry system is to prescribe drug-related items to a patient.

19 Claims, 8 Drawing Sheets

FIG. 10 ents, etc. The various components shown in the figures can
PRE-SELECTION DISPLAY OF ALERTS IN AN ORDER ENTRY SYSTEM

BACKGROUND

A physician or other caregiver may use an order entry system to prescribe drug-related items ("items") to a patient. In a typical system, a user may select an item from a list of available items. The selected item may be inappropriate for one or more reasons. For example, the item may present a danger to the patient in view of a condition that affects the patient (such as a drug allergy). Alternatively, or in addition, the item may be inappropriate because it conflicts with another drug-related item that has already been prescribed to the patient. Still other factors may contribute to the inappropriateness of an item.

An order entry system may address the above problem by presenting a pop-up alert after the physician selects the item. The pop-up alert informs the physician of a safety-related concern regarding the selected item. The physician can remove the pop-up alert by clicking on it or by deactivating it in some other manner. In some cases, the order entry system may identify multiple safety-related concerns of varying degrees of seriousness. In this case, the order entry system may present multiple such pop-up alerts. The physician may act on these pop-up alerts in sequential fashion in the manner described above. If a drug-related item is deemed a poor choice, the physician may decide to select another item. If this alternative item is likewise problematic, the physician may be confronted with another series of pop-up alerts.

The physician may find the above-described prescription process cumbersome and time-consuming. As a result, the physician may become frustrated with the process, leading to a phenomenon that may be referred to as "alert fatigue." The physician may address the tedium of responding to pop-up alerts by quickly de-activating pop-up alerts in rote fashion, or by adjusting the threshold of the order-entry system so that not so many pop-up alerts are presented. In either case, the physician runs the risk of overlooking a pop-up alert which notifies the physician of a serious safety-related issue.

The shortcomings identified above are not limited to the field of patient care. Other order entry systems may present similar challenges.

SUMMARY

An illustrative order-entry system is described which displays items together with visual attributes that correspond to respective context-specific alerts. The visual attributes provide pre-selection guidance to a user in choosing from among the items. In other words, the order-entry system presents the visual attributes before the user makes a selection of any item. In this manner, the user may make an informed choice without being deluged with a tedious sequence of post-selection alerts.

According to another illustrative aspect, the items that are displayed may correspond to drug-related items. In this case, one purpose of the order-entry system is to prescribe drug-related items to a patient.

According to another illustrative aspect, the visual attributes correspond to icons that can be placed in proximity to textual information associated with the respective items. In addition, or alternatively, the visual attributes correspond to at least one visual aspect of the textual information itself.

The above approach can be manifested in various types of systems, components, methods, computer readable media, data structures, and so on.

This Summary is provided to introduce a selection of concepts in a simplified form; these concepts are further described below in the Detailed Description. This Summary is not intended to identify key features or essential features of the claimed subject matter, nor is it intended to be used to limit the scope of the claimed subject matter.

The same numbers are used throughout the disclosure and figures to reference like components and features. Series 100 numbers refer to features originally found in FIG. 1, series 200 numbers refer to features originally found in FIG. 2, series 300 numbers refer to features originally found in FIG. 3, and so on.

DETAILED DESCRIPTION

This disclosure sets forth an order entry system that presents alerts to a user in advance of the user's selection from among a plurality of items. As will be explained in greater detail below, the order entry system can be applied to the task of ordering drug-related items for patients, but it not limited to this use. Nor is it limited to the general field of patient care.

This disclosure is organized as follows. Section A describes an illustrative order entry system which presents pre-selection alerts. Section B describes illustrative methods which explain the operation of the order entry system. Section C describes illustrative processing functionality that can be used to implement any aspect of the features described in Sections A and B.

Figure 10:
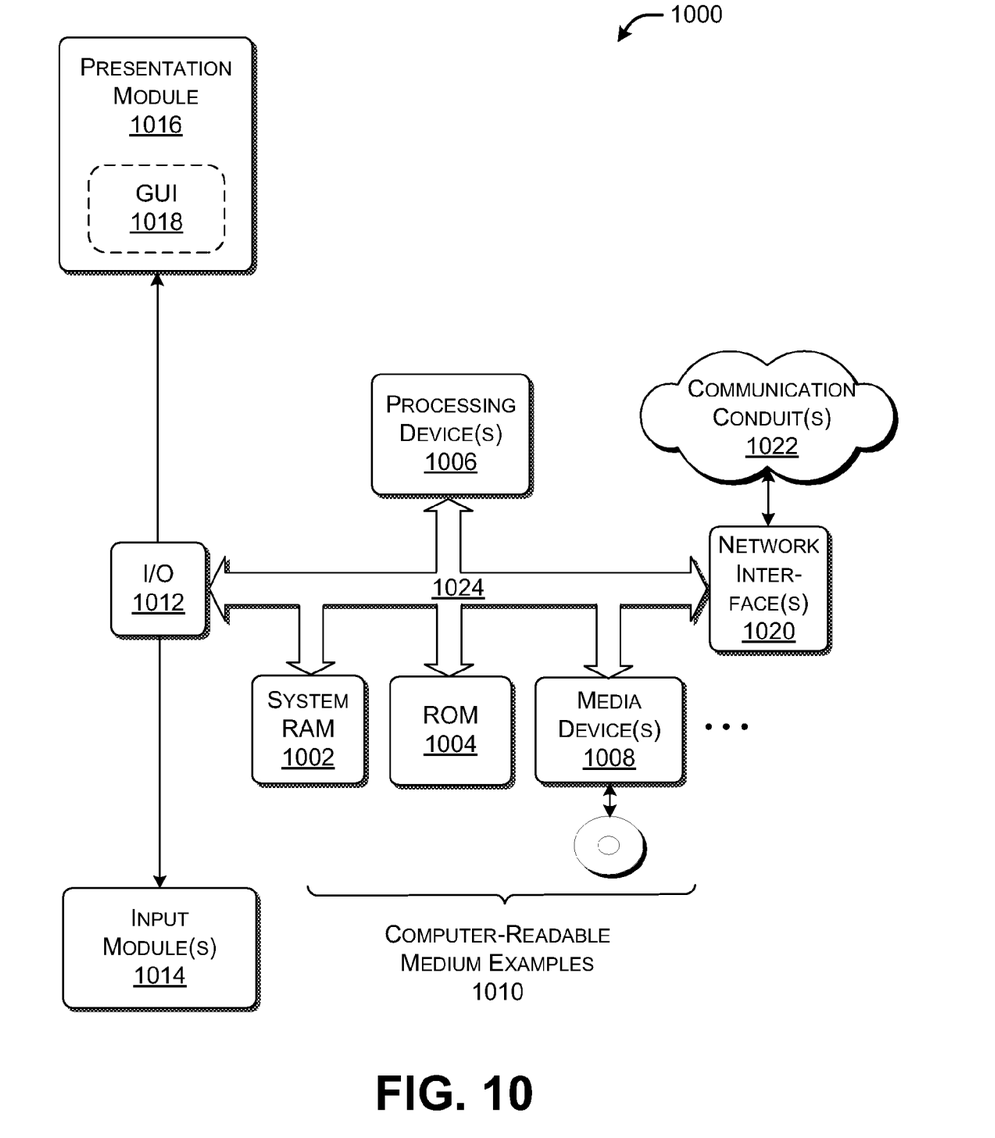
FIG. 10 shows illustrative processing functionality that can be used to implement any aspect of the features shown in the foregoing drawings.

As a preliminary matter, some of the figures describe concepts in the context of one or more structural components, variously referred to as functionality, modules, features, elements, etc. The various components shown in the figures can be implemented in any manner, for example, by software, hardware (e.g., discrete logic components, etc.), firmware, and so on, or any combination of these implementations. In one case, the illustrated separation of various components in the figures into distinct units may reflect the use of corresponding distinct physical components. Alternatively, or in addition, any single component illustrated in the figures may be implemented by plural physical components. Alternatively, or in addition, the depiction of any two or more separate components in the figures may reflect different functions performed by a single physical component. FIG. 10, to be discussed in turn, provides additional details regarding one illustrative implementation of the functions shown in the figures.

Other figures describe the concepts in flowchart form. In this form, certain operations are described as constituting distinct blocks performed in a certain order. Such implementations are illustrative and non-limiting. Certain blocks described herein can be grouped together and performed in a single operation, certain blocks can be broken apart into plural component blocks, and certain blocks can be performed in an order that differs from that which is illustrated herein (including a parallel manner of performing the blocks). The blocks shown in the flowcharts can be implemented by software, hardware (e.g., discrete logic components, etc.), firmware, manual processing, etc., or any combination of these implementations.

As to terminology, the phrase "configured to" encompasses any way that any kind of functionality can be constructed to perform an identified operation. The functionality can be configured to perform an operation using, for instance, software, hardware (e.g., discrete logic components, etc.), firmware etc., and/or any combination thereof.

The term "logic" encompasses any functionality for performing a task. For instance, each operation illustrated in the flowcharts corresponds to logic for performing that operation. An operation can be performed using, for instance, software, hardware (e.g., discrete logic components, etc.), firmware, etc., and/or any combination thereof.

A. Illustrative Systems

Figure 1:
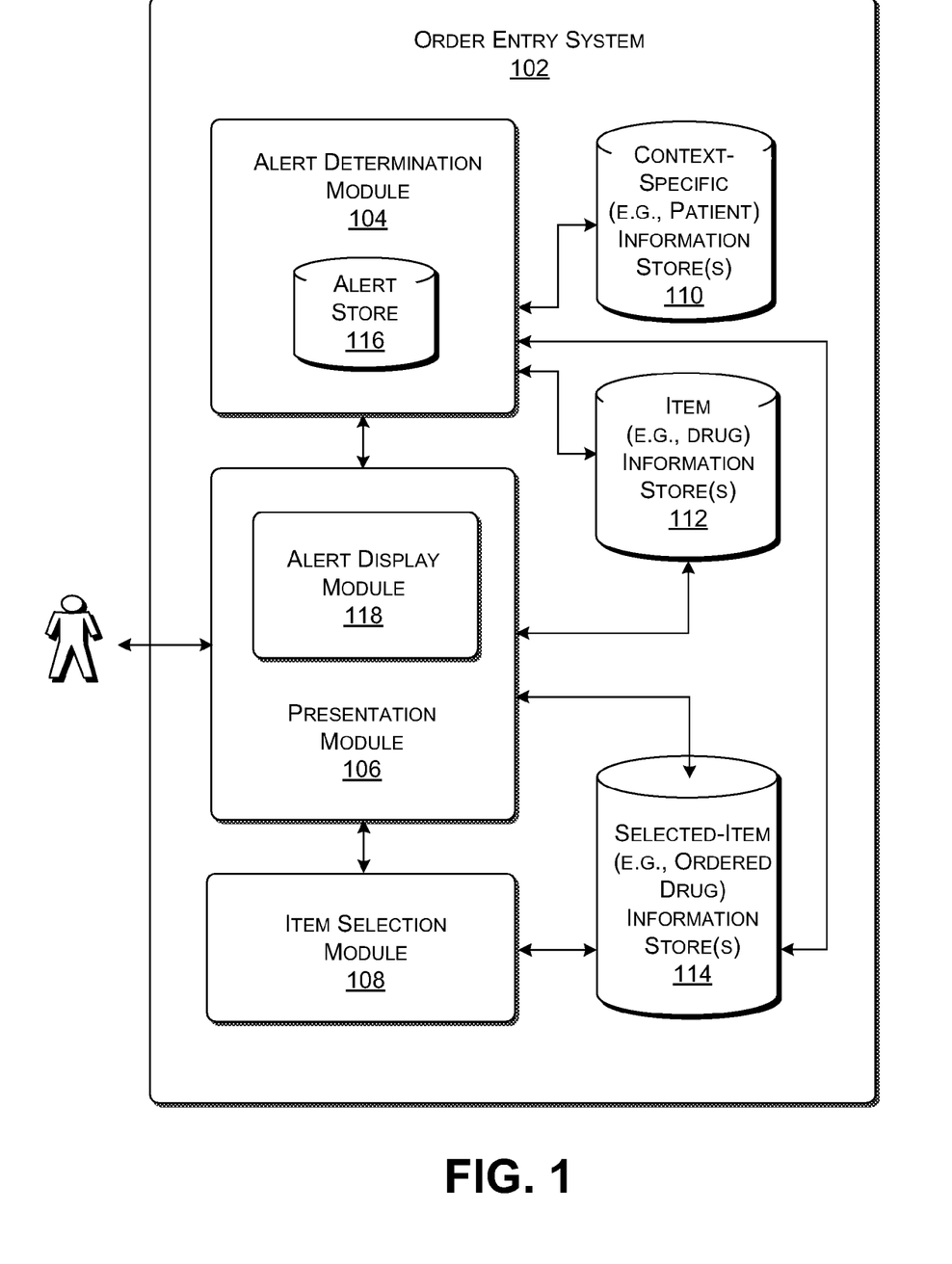
FIG. 1 shows an illustrative electronic order entry system for making selections among items, as facilitated by pre-selection alerts.

FIG. 1 shows an electronic order entry system 102 ("order entry system") for use in ordering items. In one case, a user can use the order entry system 102 to prescribe drug-related items to patients. In this context, the user may correspond to a physician or other caregiver (or any other authorized person or entity). The user may order the drug-related items by selecting the drug-related items from a collection of available drug-related items.

The order entry system 102 can be applied to other scenarios in which a user selects items from a collection of available items, assisted by alerts. In another example, the order entry system 102 can be used by a caregiver to subscribe other types of heath care articles or services to a patient. In another example, the order entry system 102 can be used by an architect to select materials for use in constructing a building. In another example, the order entry system 102 can be used by a hazardous material specialist to select materials for use in a workplace or other setting. In another example, an agricultural specialist can use the order entry system 102 to select fertilizers and the like to apply to the environment, and so on. Many more applications are possible. Nevertheless, to facilitate explanation, the ensuing description will be framed primarily in the context of the prescription of drug-related items ("items" for brevity) to patients.

The order entry system 102 includes (or can be conceptualized to include) a collection of components for use in performing its functions: an alert determination module 104; a presentation module 106; and an item selection module 108.

As described above, these components may correspond to distinct modules for performing respective tasks or may correspond to identifiable functions performed by a more-encompassing module (or modules).

By way of overview, the alert determination module 104 determines alerts associated with available items. The presentation module 106 displays items and accompanying alerts. The item selection module 108 manages the user's selection of one or more of the items that are displayed, thereby prescribing these items for use by an identified patient. More specifically, the presentation module 106 displays the alerts in association with the items before the user makes a selection from among the items. Accordingly, the alerts serve as pre-selection guidance to the user in choosing among the items.

For instance, assume that the order entry system 102 displays three items which are commonly used to treat an ailment from which a patient suffers. Yet suppose that two of these three items are tagged with negative safety-related alerts, but not the third item. The user may respond by choosing the last-mentioned item that is not associated with a negative alert. By providing the alerts to the user at the outset, prior to making a selection, the user need not be burdened with one or more post-selection alerts. Hence, the order entry system 102 can help reduce alert fatigue in the user. Further, since the user is not burdened by a large number of post-selection alerts, the user may be less apt to overlook significant alerts. (More specifically, in one case, the order entry system 102 entirely eliminates all post-selection alerts. In another implementation, the order entry system 102 still generates post-selection alerts if the user selects items that are problematic for any reason, but the number of these post-selection alerts can be expected to be manageable; this is because the user can be expected to select, in many cases, items that do not have safety-related concerns, as revealed by the pre-selection alerts.)

With the above introduction, the individual components of FIG. 1 will now be described in greater detail, starting with the alert determination module 104. The alert determination module 104 can rely on factor information in determining alerts associated with individual items. Broadly, the factor information encompasses any type of consideration that has a bearing on whether it is appropriate to generate an alert, and if so, what type of alert is to be generated. Without limitation, FIG. 1 shows three representative sources of factor information provided in stores 110, 112 and 114. These stores (110, 112, 114) may represent physically distinct repositories of information or may represent different fields that are provided in one or more physical repositories of information.

A first source of factor information corresponds to context-specific information provided in one or more stores 110. The context information corresponds to any information associated with a context in which items are being selected which may have a bearing on the appropriateness of the items. In the drug-related scenario, the context-specific information corresponds to patient information. The patient information may encompass any information regarding a patient which may have a bearing on what types of items may be safely prescribed to the patient. For example, the patient information may encompass the patient's drug allergies. The patient information may also identify any other characteristic of the patient (including the patient's family history) that may have a bearing on the suitability of items for this patient. For example, the patient information can identify whether a patient is pregnant or whether the patient suffers from a particular disease, as this information has a bearing on what items are appropriate to prescribe to this patient. Insofar as the alerts are based, in part, on patient information, the alerts may be regarded as context-specific in nature. (The order entry system 102 can maintain appropriate safeguards to ensure the privacy of the patient's information. Further, the patient may remain in control of his or her information, managing the creation, modification, dissemination, and destruction of this information.)

A second source of information corresponds to item information provided in one or more stores 112. The item information can encompass a wide range of information that has a bearing on the safety-related characteristics of available items. For example, in the caregiving scenario, the item information for a particular item may identify that this item presents a risk for patients who are also taking another type of medication. In addition, or alternatively, the item information may specify that the item presents a risk for patients who suffer from certain ailments or who have other identifiable conditions.

A third source corresponds to selected-item information provided in one or more stores 114. In the caregiving scenario, the selected-item information identifies any items that have been previously prescribed to a patient (wherein the prescription is still active). The selected-item information can be used in conjunction with the item information to indicate potentially dangerous interactions among items.

The three sources of factor information described above are illustrative and non-exhaustive. Other applications of the order entry system 102 may rely on different types of factor information.

The alert determination module 104 operates on the factor information to determine safety-related concerns associated with a list of available items. It performs this task in a manner which will be described more fully in Section B (in connection with FIG. 8). By way of overview, the alert determination module 104 can enumerate the safety-related concerns associated with each item in the list of available items. In some cases, an item may have plural safety-related concerns associated therewith. In other cases, an item may have one or no safety-related concerns associated therewith. Each safety-related concern (or an indication of the absence thereof) is referred to as an alert component herein. For example, a safety-related concern can be based on any type of potential problem, such as a drug-drug interaction, duplicate therapy concern, contraindication concern, drug-allergy reaction, side effect reaction, and so on.

The alert determination module 104 can also identify an alert level associated with each alert component. The alert level identifies the degree of severity of a safety-related concern (or the absence thereof). For example, an item will receive a relatively high alert level if the patient is allergic to that item. The alert determination module 104 can assess the severity of a safety-related concern based on a knowledge base of rules, in combination with insight gathered from the factor information (provided by stores 110, 112, and 114).

After assessing the alert components associated with a particular item, the alert determination module 104 can identify the alert component posing the greatest safety-related concern (or at least a relatively high safety-related concern). The alert determination module 104 may use the alert component with the highest alert level to represent the alert as a whole. For example, assume that there are three safety-related concerns associated with prescribing a particular item to a patient, assigned alert levels 1, 2, and 4 (where alert level 4 represents the highest severity level). The alert determination module 104 may associate alert level 4 with the alert for this item. In general, the alert determination module 104 can store all information regarding alerts within one or more alert stores 116.

The presentation module 106 displays the items along with alerts associated with the items. More particularly, in one case, the presentation module 106 can present textual information (or some other type of visual representation) that describes the items, such as by displaying a list of names associated with the items. The presentation module 106 also presents visual attributes that convey the alerts associated with the items. The operation of the presentation module 106 can thus be described in abstract terms in the context of the presentation of items and alerts, or more specifically, in terms of the presentation of textual information and accompanying visual attributes.

An alert display module 118 governs the display of visual attributes. In one case, the visual attributes may correspond to icons that are placed in physical proximity to textual information associated with the items. Alternatively, or in addition, the visual attributes may correspond to some aspect of the textual information itself. For example, the alert display module 118 can convey an alert by displaying the text of an item in a particular color, by bolding the text, by changing the size of the text, by underling the text, by italicizing the text, and so on, or by employing any combination of these strategies. Still other ways of conveying the visual attributes are possible. Further, audible alerts can be used instead of, or to supplement, visual alerts, e.g., by providing an audible announcement of those items that present safety-related concerns.

More specifically, in one implementation, the alert display module 118 can select a visual attribute which represents the safety-related concern having the highest severity identified by the alert determination module 104. For example, suppose that a particular item is a poor choice because the patient is allergic to this item. Also assume that the item is a poor choice because it provides redundant therapy for another item that the patient is currently taking, but that this consideration does not otherwise raise a safety concern. In this case, the alert display module 118 can select a visual attribute that represents the drug allergy safety concern. As will be described, the presentation module 106 can provide additional mechanisms which allow the user to investigate the full wealth of safety-related concerns associated with a particular item. If there are no safety-related concerns for an item, the alert display module 118 can optionally select a visual attribute which communicates this fact.

Figure 2:
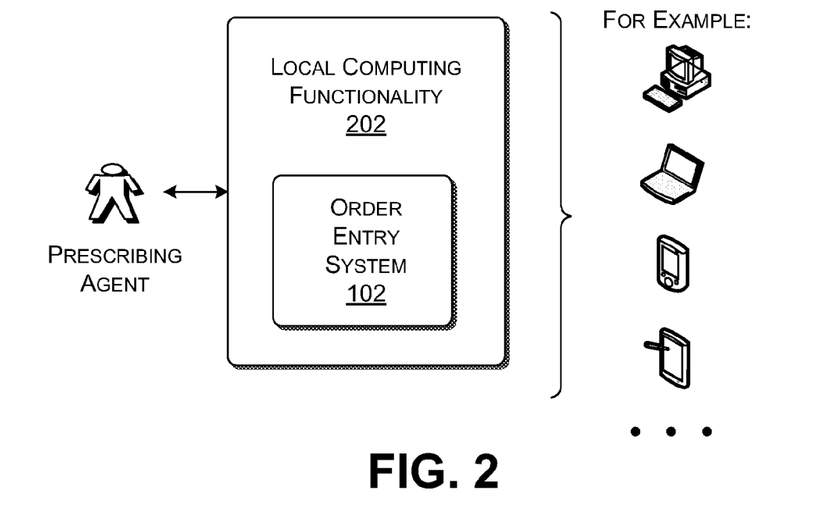
FIG. 2 shows an illustrative stand-alone implementation of the order entry system of FIG. 1.
Figure 3:
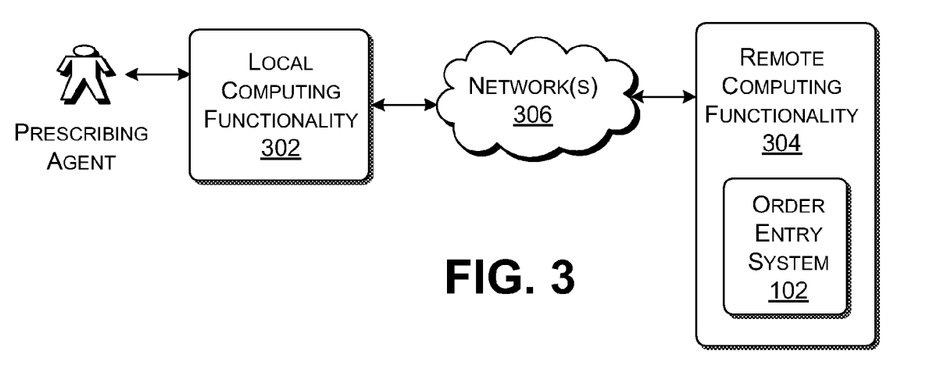
FIG. 3 shows one illustrative implementation of the order entry system of FIG. 1 that uses remote computing functionality.
Figure 4:
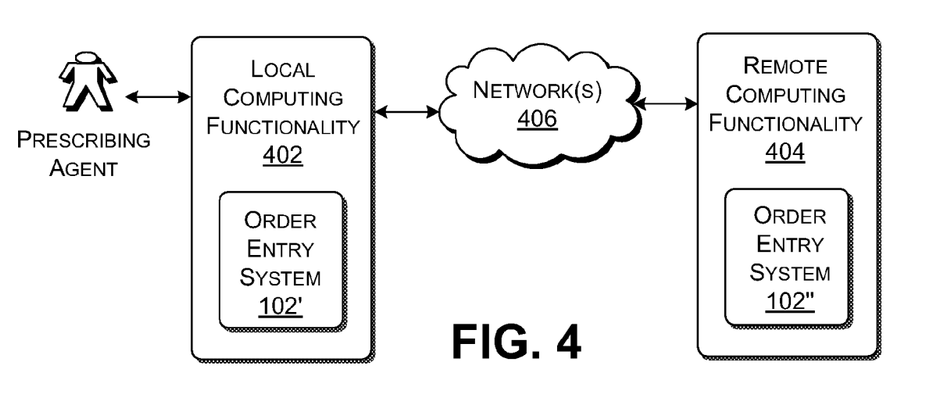
FIG. 4 shows another illustrative implementation of the order entry system of FIG. 1 that uses remote computing functionality.

FIGS. 2-4 show three representative implementations of the order entry system 102 of FIG. 1. These three implementations are not exhaustive; other implementations are possible.

FIG. 2 shows a stand-alone implementation of the order entry system 102 of FIG. 1. In this case, a prescribing agent interacts with local computing functionality 202, and this local computing functionality 202 provides all the resources of the order entry system 102. The local computing functionality 202 can correspond to any type of functionality for performing the above-described functions, such as a personal desktop computing device, a laptop computing device, a personal digital assistant (PDA) type computing device, a stylus-type computing device, a mobile phone type computing device, and so on. In these applications, one or more processors can implement the above-described functions when executing computer readable instructions. Alternatively, or in addition, the local computing functionality 202 can represent a custom device which includes components that are particularly tailored to perform the above-described functions.

FIG. 3 shows another implementation of the order entry system 102. Here, a prescribing agent uses local computing functionality 302 to interact with remote computing functionality 304 via a network 306. The remote computing functionality 304 may provide all the resources which implement the order entry system 102. In this case, the local computing functionality 302 may represent any of the types of devices described above in connection with FIG. 2. The remote computing functionality can represent any type of remote processing infrastructure, such as one or more server-type computers in cooperation with one or more data stores (and potentially other types of data processing equipment). The resources of the remote computing functionality 304 can be provided at a single location or can be distributed over plural locations. The network 306 can represent a local area network, a wide area network (e.g., the Internet), or some combination thereof. In one concrete (but non-limiting) scenario, FIG. 3 can represent the case in which the prescribing agent uses any type of local computing functionality 302 to access the functionality of the order entry system 102 as a web-type of application, e.g., via the Internet or a proprietary local area network, etc.

FIG. 4 shows another implementation of the order entry system 102. Here again, a prescribing agent uses local computing functionality 402 to interact with remote computing functionality 404 via a network 406 (where these components can be implemented in the manner described above). In this case, however, the resources of the order entry system 102 can be distributed between the local computing functionality 402 and the remote computing functionality 404. Namely, the local computing functionality implements a first part 102' of the order entry system 102, while the remote computing functionality 404 implements a second part 102" of the order entry system 102. In one concrete (but non-limiting) scenario, FIG. 4 can correspond to the case in which parts of the functionality used to calculate and display the alerts are provided by the local computing functionality 402, while the stores (110, 112, 114) that provide the factor information are provided by the remote computing functionality 404.

Figure 5:
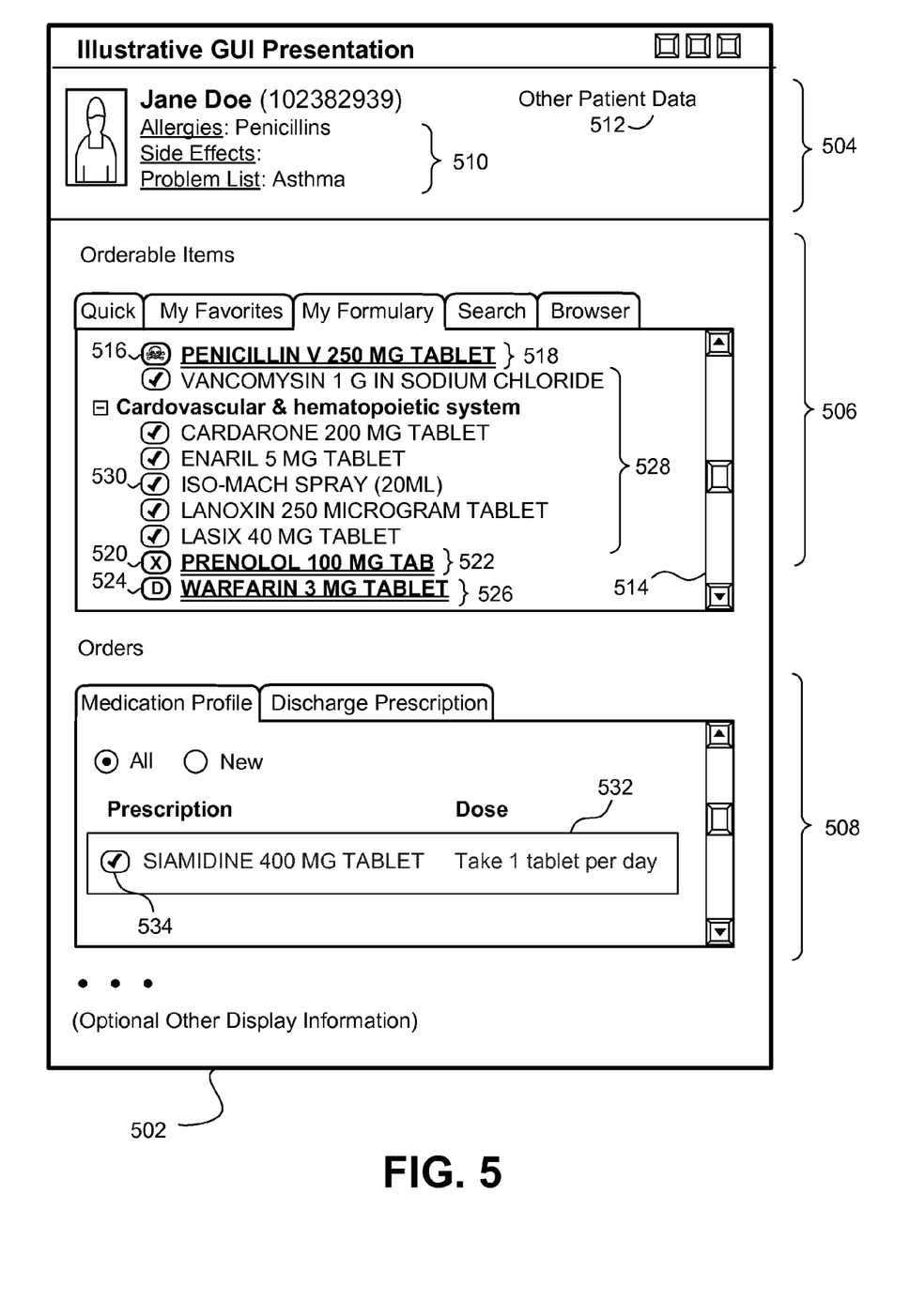
FIG. 5 shows an illustrative graphical user interface presentation that may be generated by the order entry system of FIG. 1; this presentation particularly shows visual attributes that can be used to convey alerts to the user before the user chooses among the items.

FIG. 5 shows one illustrative graphical user interface (GUI) presentation 502 that can be generated by the order entry system 102 of FIG. 1. In this case, the order entry system 102 is applied to the task of prescribing drug-related items to patients. The GUI presentation 502 allows the user to review available items that can be prescribed to a patient and then select one or more items (thereby ordering the items).

The GUI presentation 502 includes multiple main sections, including a patient profile section 504, an orderable item section 506, and an ordered item section 508. Other GUI presentations can convey the same information in different ways. For example, other GUI presentations can adopt different main sections compared to that shown in FIG. 5. In addition, or alternatively, other GUI presentations can vary the appearance (e.g., "look and feel") and functionality of the sections shown in FIG. 5.

The patient profile section 504 provides information regarding the patient, the hypothetical Jane Doe. The information presented in the patient profile section 504 may correspond to the patient information provided in the store 110 of FIG. 1. The patient information may identify various characteristics 510 of the patient that may have a bearing on what drug-related items can be safely prescribed for the patient. For example, the characteristics 510 may identify the drug allergies, side effects, and other factors that may have a bearing on the selection of items for the patient. In this particular case, the characteristics 510 indicate that the patient is allergic to penicillin and also suffers from asthma. The patient profile section 504 can also present any other patient data 512, not specifically enumerated in FIG. 5.

The orderable item section 506 provides information regarding one or more items that can be selected for the patient. The orderable item section 506 may allow a user to review available items in different operational modes. For example, in a "My Formulary" mode, the user can review a user-selected master list of items. In a "My Favorites" mode, the user can review a subset of items that he or she frequently prescribes to patients. Still other modes can be used to display one or more items to the user for his or her consideration.

The orderable item section 506 can present a collection of items in a list form, as indicated in the representative case of FIG. 5, or in some other format (such as a two-dimensional array format, etc.). The user can optionally navigate to different parts of the list using a scroll bar mechanism 514 or other type of navigational mechanism. The orderable item section 506 can identify the items by presenting textual information associated with the items, such as brief textual descriptions of the items.

The orderable item section 506 can convey the alerts by presenting visual attributes associated with the alerts. In the representative case of FIG. 5, the alert display module 118 can use multiple types of visual attributes to convey the alerts. For example, as one type of visual attribute, the alert display module 118 can place an icon in proximity to a textual description of an item. In addition, or alternatively, the alert display module 118 can convey an alert via one or more visual aspects of the textual description.

For example, the alert display module 118 displays an icon 516 next to an item 518 ("PENICILLIN V 250 MG TABLET"). In this case, the icon 516 represents the fact that the patient is allergic to the item 518 (as indicated in the patient profile section 504). The alert display module 118 also conveys the alert by presenting the item's corresponding textual description in bold and by underlining it. This is one representative example; in general, the alert display module 118 can convey the alert using any other type of visual aspect or combination of visual aspects of the textual information (such as color, size, and so on).

The alert display module 118 can present another type of icon 520 next to an item 522, the description of which is "PRENOLOL 100 MG TABLET." In this case, the icon 520 conveys that the item 522 may cause a problem in view of the fact the patient suffers from asthma (e.g., because the item is a beta-blocker which is contraindicated for patients who suffer from asthma). The alert display module 118 also conveys the nature of the alert via a visual aspect of the textual information associated with the item 522, such as by bolding and underlining the description.

The alert display module 118 can present another type of icon 524 next to an item 526, the description of which is "WARFARIN 3 MG TABLET." In this case, the icon 524 conveys that the item 526 conflicts with another drug-related item that is currently prescribed to the patient, namely SIAMIDINE. The alert display module 118 also conveys the nature of the alert via a visual aspect of the textual information associated with the item 526, such as by underlining the description.

The three icons described above may communicate different levels of severity. For example, icon 516 may convey the highest level of severity. The icons may include symbolic or pictorial information which is commensurate with their associated level of severity. For example, the icon 516 includes a picture of a skull and crossbones to indicate that it represents a serious safety-related concern. In this manner, the user is quickly apprised of the serious problems associated with the items, even though there may be more than one safety-related concern associated with any given alert. As will be described below, the alert display module 118 can provide various mechanisms which allow the user to explore the full wealth of alert-related information associated with any item upon request.

A group of items 528 has no safety-related concerns associated therewith. The alert display module 118 can communicate this finding using a designated type of icon, such as the representative icon 530. In this example, the icon 530 uses a check mark to indicate the absence of safety-related concerns, although any other type of symbol or pictorial representation can be used to convey the same status information. Alternatively, the alert display module 118 can entirely omit icons (and other visual attributes) for items that have no safety-related concerns.

In operation, a user can peruse the list of items in the orderable item section 506, together with their alerts. Based on this information, the user may decide to select an item that has no safety-related concerns associated with it. Or the user may decide to choose an item with a safety-related concern that is deemed acceptable. The user can investigate any item in further detail by requesting additional information regarding its alert profile (as described below). As a consequence of this approach, the user can avoid being subjected to a series of post-selection alerts in piecemeal fashion (or can at least reduce the number of post-selection alerts). Hence, the approach shown in FIG. 5 can help reduce the user's alert fatigue, while simultaneously focusing the user's attention on the high-level safety-related concerns.

The ordered item section 508 identifies the items that the user has previously selected. In this case, the user has previously selected an item 532 that bears the description "SIAMIDINE 400 MG TABLET." The alert display module 118 can also present one or more visual attributes which convey the alert status of items within the ordered item section 508. For example, the item 532 includes a check mark icon 534 which conveys that there are no identified safety-related concerns with the item 532.

In general, the alert determination module 104 operates by updating the alerts shown in FIG. 5 when the factor information (on which the alerts are based) changes in any way. For example, consider the case in which a user selects an item shown in the orderable item section 506, causing it to be displayed in the ordered item section 508. This creates a new set of selected items to be considered in assessing potential negative interactions among items. The alert display module 118 responds by displaying a new set of alerts within the orderable item section 506 and the ordered item section 508 (assuming that the alerts have changed in response to the selection of the new item).

Figure 6:
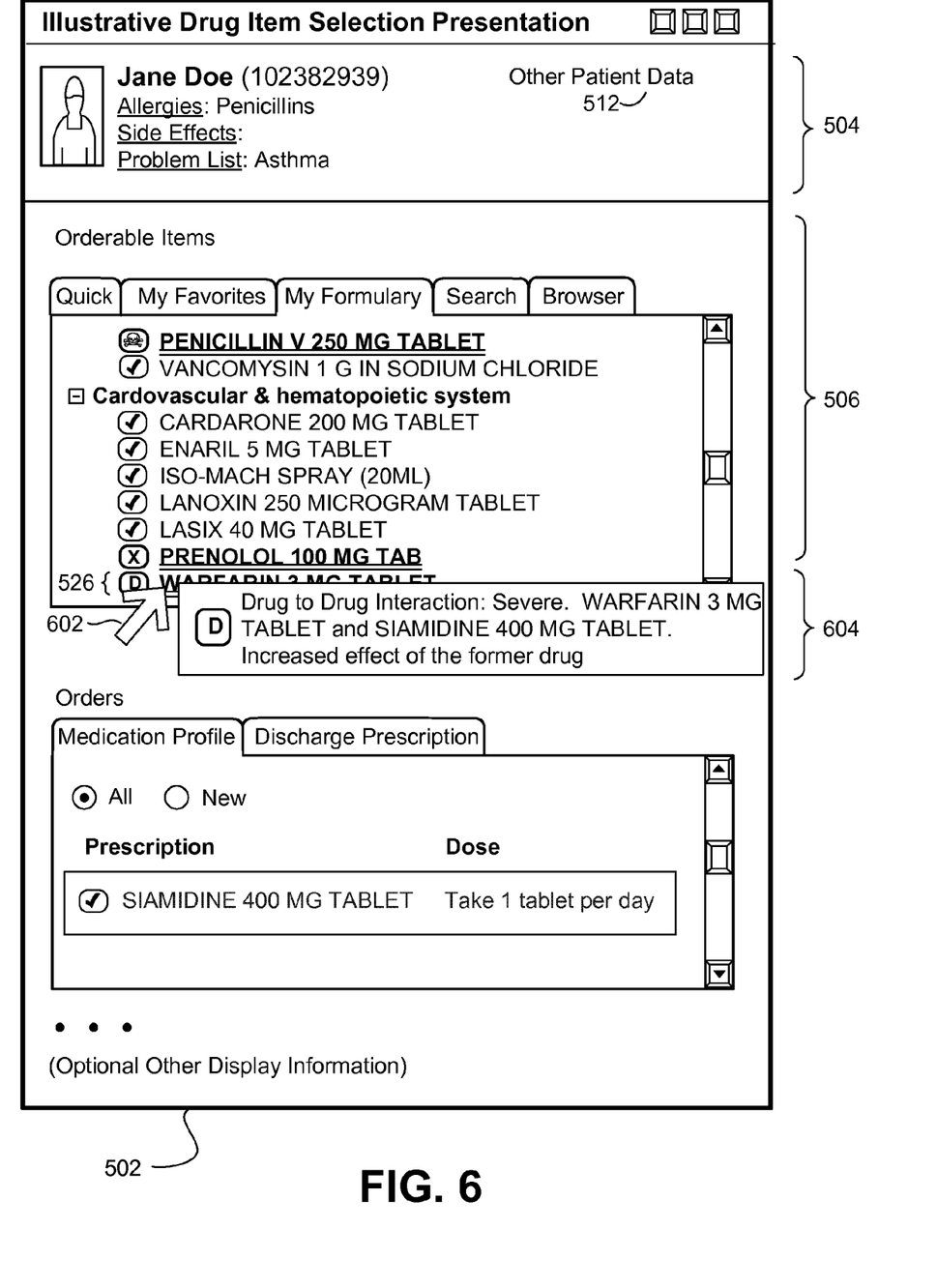
FIG. 6 shows another illustrative graphical user interface presentation that may be generated by the order entry system of FIG. 1; this presentation adds to FIG. 5 by showing descriptive information that can be displayed upon the request of the user.

FIG. 6 shows another depiction of the GUI presentation 502 of FIG. 5. Here, the figure shows that the user has positioned a cursor 602 (e.g., as controlled by a mouse device or other type of input device) over the item 526, associated with the description "WARFARIN 3 MG TABLET." In response, the alert display module 118 presents descriptive information 604 in the form of a textual overlay. The descriptive information 604 can present any type of information regarding the alert. For example, assume that the alert includes multiple alert components that represent multiple safety-related concerns. In this case, the descriptive information 604 can enumerate all the safety-related concerns associated with the item 526. The use of a mouse-over-controlled textual overlay is only one way to provide additional information; other mechanisms can be used in other implementations, such as a user-activated pop-up alert.

B. Illustrative Processes

Figure 7:
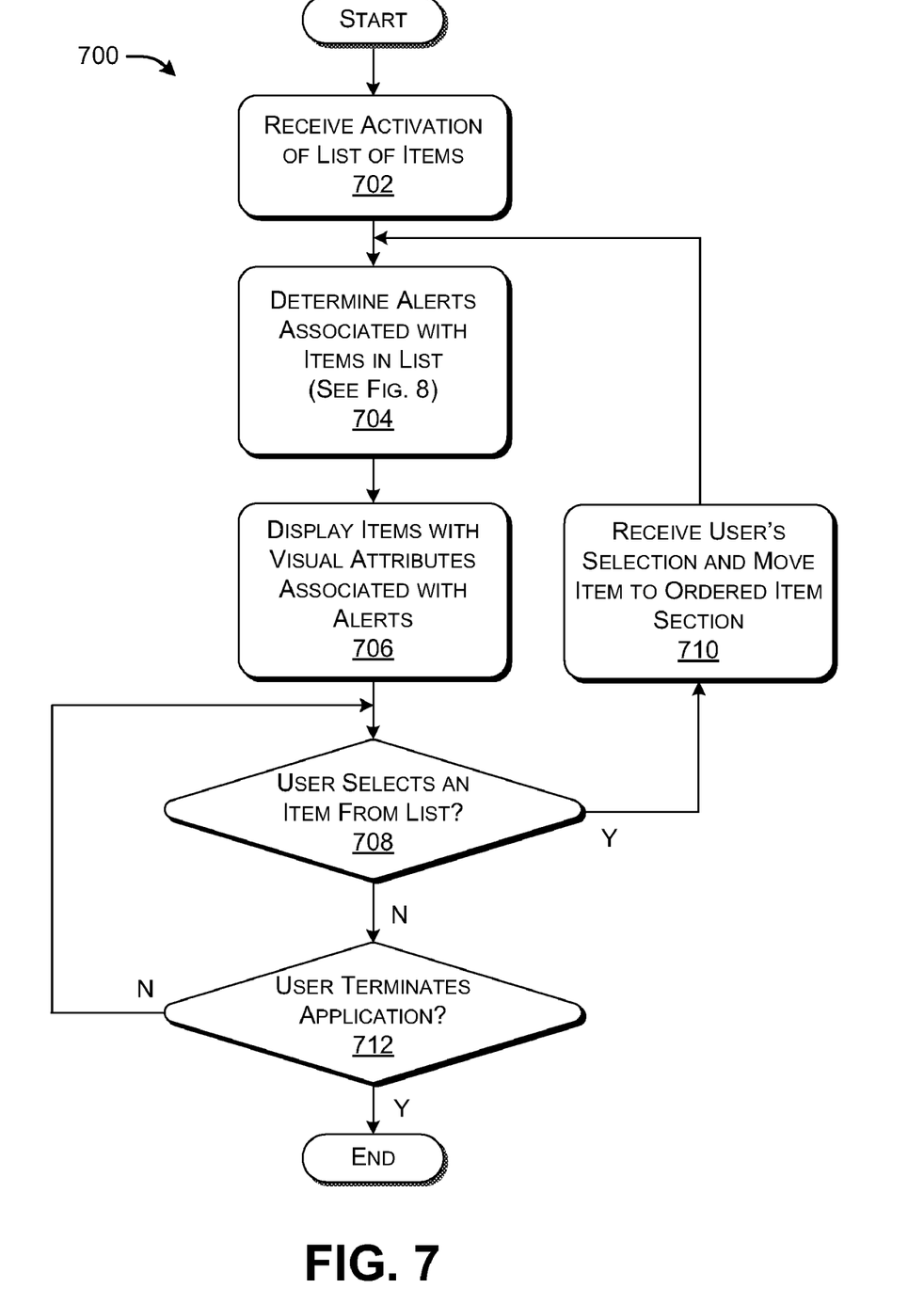
FIG. 7 shows an illustrative procedure for displaying items and accompanying alerts.
Figure 8:
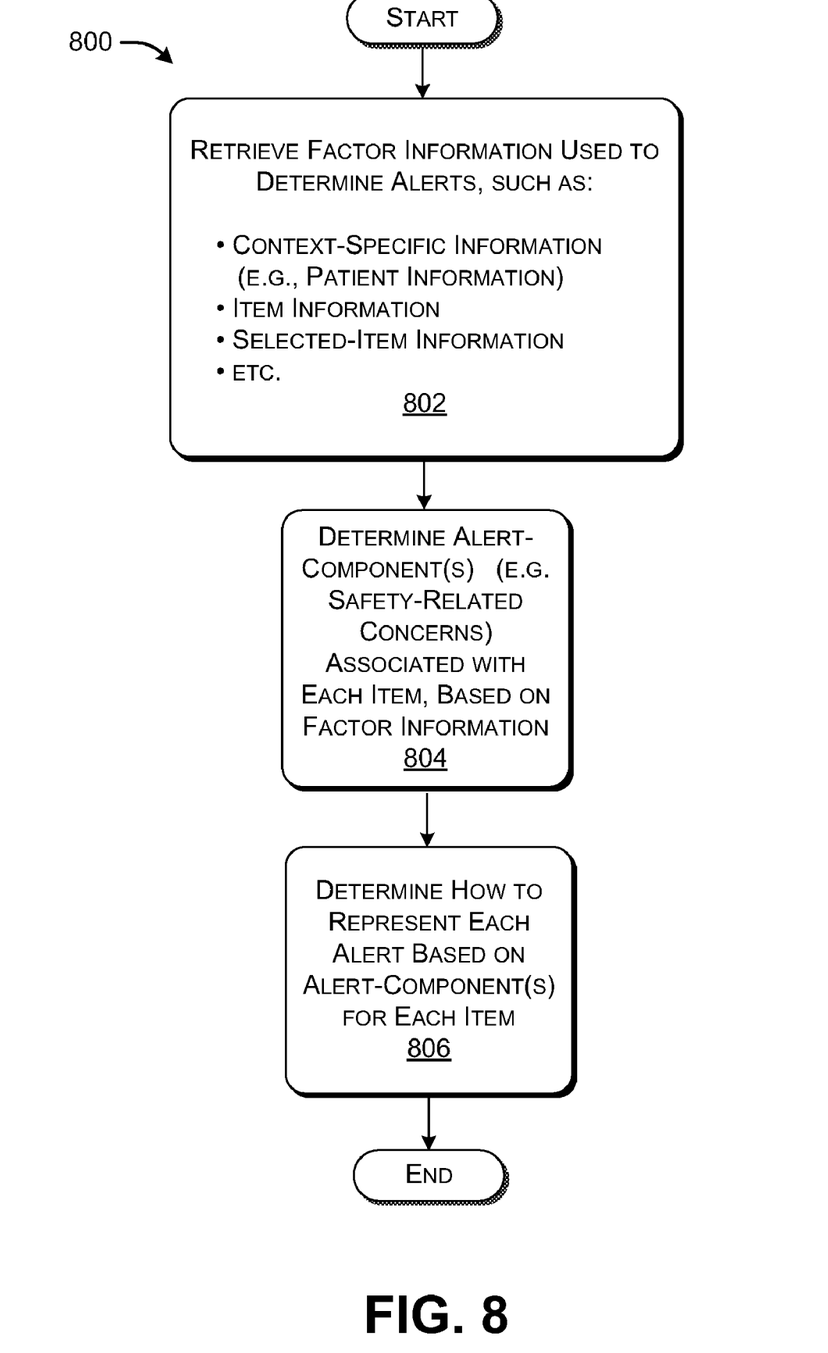
FIG. 8 shows an illustrative procedure for determining alerts in the context of the procedure of FIG. 7.
Figure 9:
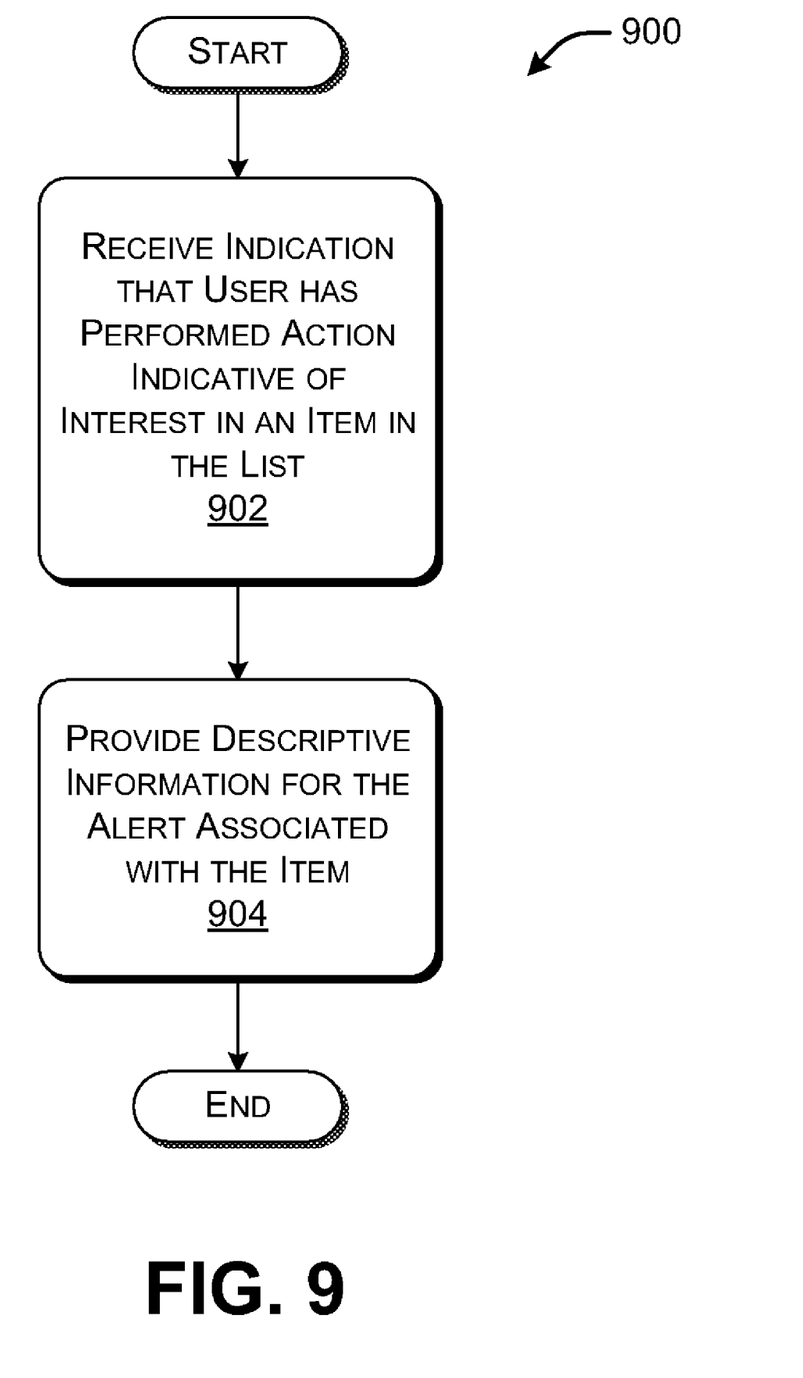
FIG. 9 shows an illustrative procedure for presenting additional descriptive information regarding an alert when requested by a user.

FIGS. 7-9 show procedures (700, 800, 900) which explain the operation of the order entry system 102 of FIG. 1 (or some other type of order entry system that embodies the concepts of FIG. 1) in flowchart form. Since the principles underlying the operation of the order entry system 102 have already been described in Section A, certain operations will be addressed in summary fashion in this section.

Starting with FIG. 7, the illustrated procedure 700 provides an overview of the operation of the order entry system 102. The operations will be described from the "perspective" of the order entry system 102.

In block 702, the order entry system 102 receives an activation of a list of items. This operation may correspond to the user selecting a presentation option in the orderable item section 506, such as by clicking on the "My Formulary" tab or the like. In another case, the order entry system 102 can automatically present a list of items without requiring the user to make any express instructions to that effect.

In block 704, the order entry system 102 determines alerts associated with the items in the list. FIG. 8 (described below) provides additional information regarding this procedure.

In block 706, the order entry system 102 display items together with visual attributes associated with the alerts that have been determined in block 704.

In block 708, the order entry system 102 determines whether the user has selected an item in the list of items. If so, in block 710, the order entry system 102 receives the user's selection. Further, the order entry system 102 may then display the selected item in the ordered item section 508 of the GUI presentation 502. The selection of an item then prompts the order entry system 102 to return to block 704, where the order entry system 102 re-determines the alerts (because the factor information that has a bearing on the alerts has now changed).

In block 712, the order entry system 102 determines whether the user has terminated the prescription operation. If so, the order entry system 102 terminates the procedure 700.

The procedure 800 of FIG. 8 provides additional information regarding one approach to determining alerts.

In block 802, the order entry system 102 retrieves factor information that is used to determine alerts. In the context of a drug prescription environment, the factor information may correspond to patient information, item information, and selected-item information. As explained above, the patient information describes the characteristics of the patient. The item information describes safety-related features of the items that are available for prescription to the patient. The selected-item information identifies items that have already been prescribed to the patient.

In block 804, the order entry system 102 determines the alert components associated with each item. This operation entails enumerating the individual safety-related concerns associated with the item, and then assigning severity levels to the safety-related concerns.

In block 806, the order entry system 102 determines how each alert will be represented to the user based on the alert components identified in block 806. Block 806 may specifically entail, for each alert, identifying the safety-related concern having the highest level of severity. The highest level of severity can then be used to represent the nature of the alert to the user. That is, the visual attribute for this alert can convey the safety-related concern with the highest level of severity. If there are no safety-related concerns for the item, the visual attribute can convey this fact.

The procedure 900 of FIG. 9 explains how a user may obtain additional information regarding any individual alert.

In block 902, the order entry system 102 receives an indication that the user has performed an action indicative of interest in an item. For example, the user may have moved a cursor so that it hovers above textual information associated with an item in the orderable item section 506.

In block 904, the order entry system 102 responds by providing descriptive information which conveys additional features of the alert associated with the item. In FIG. 6, this operation entails displaying textual information which overlays the list of items in the orderable item section 506, but the order entry system 102 can use other mechanisms to display the descriptive information (such as a pop-up panel, etc.).

C. Representative Processing Functionality

FIG. 10 sets forth illustrative electrical data processing functionality 1000 that can be used to implement any aspect of the functions described above. With reference to FIGS. 1 and 2, for instance, the type of processing functionality 1000 shown in FIG. 10 can be used to implement any aspect of the order entry system 102. In one case, the processing functionality 1000 may correspond to any type of computing device that includes one or more processing devices.

The processing functionality 1000 can include volatile and non-volatile memory, such as RAM 1002 and ROM 1004, as well as one or more processing devices 1006. The processing functionality 1000 also optionally includes various media devices 1008, such as a hard disk module, an optical disk module, and so forth. The processing functionality 1000 can perform various operations identified above when the processing device(s) 1006 executes instructions that are maintained by memory (e.g., RAM 1002, ROM 1004, or elsewhere). More generally, instructions and other information can be stored on any computer readable medium 1010, including, but not limited to, static memory storage devices, magnetic storage devices, optical storage devices, and so on. The term computer readable medium also encompasses plural storage devices. The term computer readable medium also encompasses signals transmitted from a first location to a second location, e.g., via wire, cable, wireless transmission, etc.

The processing functionality 1000 also includes an input/output module 1012 for receiving various inputs from a user (via input modules 1014), and for providing various outputs to the user (via output modules). One particular output mechanism may include a presentation module 1016 and an associated graphical user interface (GUI) 1018. The processing functionality 1000 can also include one or more network interfaces 1020 for exchanging data with other devices via one or more communication conduits 1022. One or more communication buses 1024 communicatively couple the above-described components together.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A method for presenting alerts using an electronic order entry system, comprising:
   determining alerts associated with a plurality of items as a function of an identified context prior to receiving a user selection of an item from the plurality of items;
   displaying the items together with visual attributes that correspond to the respective alerts; and
   receiving a user selection from among the items that are displayed and adding the selection to a set of selected items, the visual attributes providing pre-selection guidance to the user in choosing from among the items.

2. The method of claim 1, wherein the items correspond to respective drug-related items.

3. The method of claim 1, further comprising receiving factor information, wherein said determining of the alerts is based on the factor information.

4. The method of claim 3, wherein the items correspond to respective drug-related items, wherein the factor information comprises:
   patient information that identifies patient-related characteristics associated with an identified patient, the patient information establishing the identified context;
   item information that identifies safety-related characteristics of the drug-related items; and
   selected-item information that identifies any prior selection of a drug-related item for use by the patient.

5. The method of claim of claim 3, wherein said determining further comprises determining, for an item, at least one alert component based on the factor information, an alert associated with the item being based on said at least one alert component.

6. The method of claim 5, wherein said at least one alert component comprises two or more alert components, each alert component having a respective alert level, and wherein the alert that is determined for the item is based on an alert level that is assessed as having a highest level of severity among alert levels associated with said two or more alert components.

7. The method of claim 1, wherein said displaying comprises displaying textual information that describes the items, wherein each item has at least one visual attribute associated therewith.

8. The method of claim 7, wherein a visual attribute associated with an item corresponds to an icon that is placed in proximity to textual information associated with the item.

9. The method of claim 7, wherein a visual attribute associated with an item corresponds to a visual aspect of textual information associated with the item.

10. The method of claim 1, further comprising, in response to receiving the user selection, updating the respective alerts associated with the items.

11. The method of claim 1, further comprising:
   receiving an indication that the user has performed an action indicative of interest in a displayed item, the indication received while the items are displayed and either prior to receiving the user selection or after receiving the user selection; and
   providing, in response to receiving the indication, descriptive information regarding an alert that is associated with the item.

12. An electronic order entry system, comprising:
   an alert determination module configured to determine alerts associated with a plurality of items, each alert being associated with one or more alert components;
   a presentation module configured to display the items together with visual attributes that correspond to the respective alerts prior to receiving a user selection of an item from the plurality of items; and
   an item selection module configured to receive a user selection from among the items that are displayed and adding the selection to a set of selected items,
   the visual attributes representing alert components associated with the alerts having highest assessed levels of severity,
   the visual attributes providing pre-selection guidance to the user in choosing from among the items.

13. The electronic order entry system of claim 12, wherein the presentation module is configured to display textual information that describes the items, wherein each item has at least one visual attribute associated therewith.

14. The electronic order entry system of claim 13, wherein a visual attribute associated with an item corresponds to an icon that is placed in proximity to textual information associated with the item.

15. The electronic order entry system of claim 13, wherein a visual attribute associated with an item corresponds to a visual aspect of textual information associated with the item.

16. The electronic order entry system of claim 12, wherein the electronic order entry system is implemented as local computing functionality.

17. The electronic order entry system of claim 12, wherein the electronic order entry system is implemented by local computing functionality in cooperation with remote computing functionality, wherein the local computing functionality is coupled to the remote computing functionality via a network.

18. A media device for storing computer readable instructions, the computer readable instructions providing an electronic order entry system when executed by one or more processing devices, the computer readable instructions comprising:

presentation module logic configured to present a graphical user interface on a display, wherein the graphical user interface displays prior to receiving a user selection of a drug-related item from a plurality of drug-related items:

textual information regarding the plurality of drug-related items that may be prescribed to an identified patient; and visual attributes corresponding to alerts associated with the drug-related items, wherein the alerts are based on:

patient information that identifies patient-related characteristics associated with the identified patient;

item information that identifies safety-related characteristics of the drug-related items; and selected-item information that identifies any prior selection of a drug-related item for use by the patient, the visual attributes providing pre-selection guidance to a user in choosing from among the items; and wherein the graphical user interface provides an orderable item section that identifies the drug-related items that can be selected by a user; and an ordered item section that identifies any drug-related item that has been selected by the user.

19. The media device of claim 18, wherein any textual information presented in either the orderable item section or the ordered item section is accompanied by at least one visual attribute.

* * * * *